United States Patent
Zhong et al.

(10) Patent No.: US 6,667,029 B2
(45) Date of Patent: Dec. 23, 2003

(54) STABLE, AQUEOUS CATIONIC HYDROGEL

(75) Inventors: Yuanzhen Zhong, Wayne, NJ (US); Janusz Jachowicz, Bethel, CT (US); Philip F. Wolf, Bridgewater, NJ (US); Roger L. Mc Mullen, Jr., Bloomfield, NJ (US)

(73) Assignee: ISP Investments Inc., Wilmington, DE (US)

( * ) Notice: Subject to any disclaimer, the term of this patent is extended or adjusted under 35 U.S.C. 154(b) by 193 days.

(21) Appl. No.: 09/781,505

(22) Filed: Jan. 12, 2001

(65) Prior Publication Data

US 2001/0016189 A1 Aug. 23, 2001

Related U.S. Application Data

(63) Continuation-in-part of application No. 09/349,011, filed on Jul. 7, 1999, now abandoned.

(51) Int. Cl.[7] .................. A61K 7/075; A61K 31/79; C08F 226/10
(52) U.S. Cl. ................ 424/70.22; 424/70.1; 424/70.11; 424/70.15; 424/70.16; 526/264
(58) Field of Search .................. 424/70.1, 70.11, 424/70.15, 70.16; 526/264

(56) References Cited

U.S. PATENT DOCUMENTS

| | | | | |
|---|---|---|---|---|
| 4,065,607 A | * | 12/1977 | Kurowsky | 526/49 |
| 5,045,617 A | * | 9/1991 | Shih et al. | 526/264 |
| 5,180,804 A | * | 1/1993 | Niessner et al. | 528/500 |
| 5,635,169 A | * | 6/1997 | Blankenburg et al. | 424/70.15 |
| 5,663,258 A | * | 9/1997 | Zhong et al. | 526/264 |
| 5,717,045 A | * | 2/1998 | Tseng | 526/264 |
| 5,844,041 A | * | 12/1998 | Anderson et al. | 524/548 |

* cited by examiner

*Primary Examiner*—Sabiha Qazi
(74) *Attorney, Agent, or Firm*—Walter Katz; William J. Davis; Marilyn J. Maue

(57) ABSTRACT

A stable, aqueous cationic hydrogel of, by weight, 1–50% of a crosslinked cationic copolymer of 5–95% vinylpyrrolidone (VP) and 5–95% 3-dimethylaminopropyl(meth)acrylamide (DMAPMA) monomers, a crosslinking agent in an amount of 0.05–1% of said monomers, and water is described. The hydrogel has a pH of about 10 and a Brookfield viscosity of about 650 (Model DV-II+, RV spindle #3, speed 10 rpm); it can increase its viscosity by up to 40× at a pH of 3–9 and absorb up to 200× its weight of water. The hydrogel also can effectively condition hair even in the presence of an anionic surfactant.

13 Claims, 4 Drawing Sheets

STABLE, AQUEOUS CATIONIC HYDROGEL

CROSS-REFERENCE TO RELATED PATENT APPLICATION

This is a continuation-in-part of U.S. Pat. Ser. No. 09/349,011, filed Jul. 7, 1999 now abandoned, by the same inventors and entitled, "Crosslinked Cationic Microgels, Process for Making Same and Hair Care Compositions Therewith".

BACKGROUND OF THE INVENTION

1. Field of the Invention

This invention relates to hydrogels, and, more particularly, to stable, aqueous, crosslinked cationic hydrogels which are effective viscosity modifiers and swelling agents, and can function as conditioners in anionic surfactant-containing shampoo formulations.

2. Description of the Prior Art

Polymeric crosslinked polyacrylic acid thickeners have been used to modify the physical form, function and aesthetics of personal care formulations. However, such anionic hydrogels do not maintain their thickener action at a low pH; also they are not compatible in a cationic formulation.

Similarly, Aizawa, T. et al, in U.S. Pat. No. 5,338,815, described the preparation of fine particulate crosslinked N-vinylamide homo- and co-polymers, particularly poly-N-vinylformamide and poly-N-vinylacetamide, which had thickening properties; however, only in neutral water, (pH 6–8).

Other references of interest in this art are U.S. Pat. Nos. 5,321,110; 5,603,926; 5,663,258 and 5,684,105; Y. Zhong and P. Wolf, Hydrogel Prepared from Crosslinked Vinyl Pyrrolidone and Vinyl Acetate Copolymer, Polymer Reprints 1997,38 (2), p. 578; and Y. Zhong and P. Wolf, Swelling Properties of Crosslinked Vinylpyrrolidone Homopolymers and Vinylpyrrolidone/Vinyl Acetate Copolymers, Polymer Reprints 1998,39 (2), p. 461.

Accordingly, it is desired to provide a stable, aqueous crosslinked (XL) cationic hydrogel which is an effective viscosity modifier, and capable of adsorbing large amounts of water per weight of polymer, which is advantageous for hair thickening, conditioning and styling, in formulations having an anionic surfactant, across a wide pH range including low pHs.

These and other objects and features of the invention will be made apparent from the following description thereof.

IN THE DRAWINGS

Figure 4:
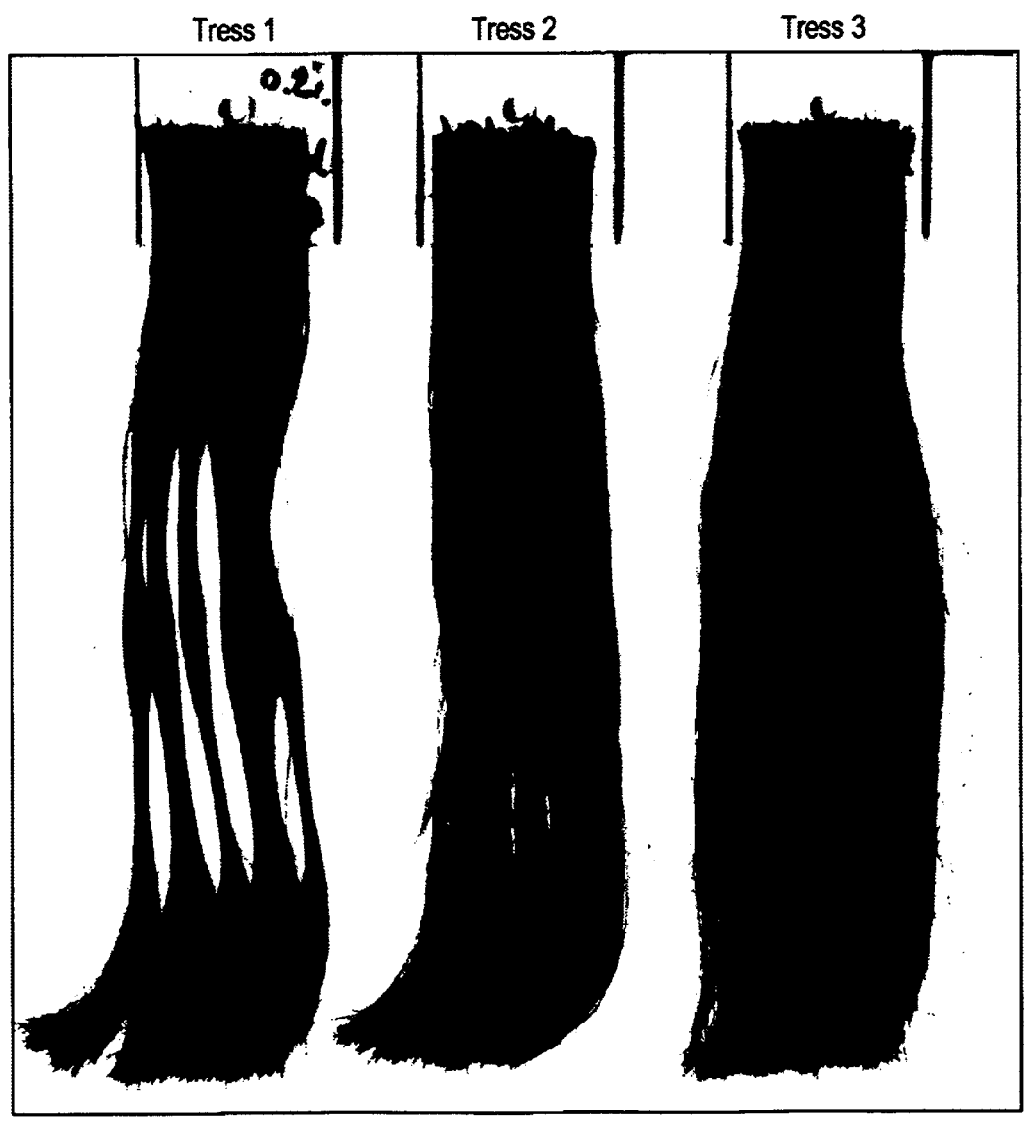

FIG. 4 presents dry hair tresses after the combing experiment. The fibers were treated with shampoo containing the cationic hydrogels of this invention (Sample #1, Tress 1, Sample #2, Tress 2) and control shampoo without conditioning agents (Tress 3).

SUMMARY OF THE INVENTION

What is described herein is a stable, aqueous cationic hydrogel comprising, by weight, 1–50% of a crosslinked cationic copolymer which is a blend of 5–95% vinylpyrrolidone (VP) and 5–95% 3-dimethylaminopropyl(meth) acrylamide (DMAPMA) monomers, a crosslinking agent in an amount of 0.05–1% of said monomers, and water, said hydrogel having a pH of about 10 and a Brookfield viscosity of about 650 (Model DV-II+, RV spindle #3, speed 10 rpm). The hydrogel can be further characterized by its increased viscosity up to 40× at a pH of 3–9; as well as being capable of absorbing up to 200× its weight of water. A hair treatment formulation containing this hydrogel can effectively condition hair even in the presence of an anionic surfactant.

In the preferred forms of the invention, the crosslinking agent is present in an amount of 0.1–0.5%, most preferably 0.2%; and the copolymer comprises 50–65% VP and 35–50% DMAPMA.

Preferably, also, the cationic hydrogel contains 5–20% of said copolymer; and in personal care formulations, 1–5%.

The cationic hydrogel of the invention, at a pH of 3–9, preferably 4–8, is useful as a viscosity modifier or swelling agent.

Personal care formulations of the invention include hair treatment compositions including about 0.01–5% by weight of the cationic hydrogel, and an anionic surfactant, for conditioning, styling and cleansing action.

The cationic hydrogel of the invention is made by an aqueous solution polymerization process. The process comprises forming a mixture of, by weight, 1–50% of a blend of 5–95% VP and 5–95% DMAPMA monomers, 0.1–0.5% crosslinker, water and initiator, polymerizing the mixture with agitation at a temperature of about 60° C. for about 1½ hours, then heating at 85° C. to complete the polymerization, and, if necessary adding water periodically to reduce the solids content of the product, and, optionally, homogenizing the resulting hydrogel product.

DETAILED DESCRIPTION OF THE INVENTION

The composition of the XL-PVP/DMAPMA copolymer of the cationic hydrogel comprises, by weight:

|  | Suitable | Preferred | Optimum |
| --- | --- | --- | --- |
| VP | 5–95 | 40–70 | 50–65 |
| DMAPMA | 5–95 | 30–60 | 35–50 |

During the polymerization reaction, the crosslinker level suitably is about 0.01–5%, preferably about 0.1–2%, and optimally about 0.2%, based on the total weight of monomers.

Suitable crosslinkers include pentaerythritol triallyl ether (PTE) and methylene-bis-acrylamide (BIS).

During the polymerization reaction, the total initial monomer level suitably is about 1–50%, preferably about 5–40%, and optimally about 15–30%.

Suitable initiators for the polymerization reaction include tertiary butyl peroxy pivalate (Lupersol® 11) and tertiary amyl peroxy pivalate (Lupersol®554).

The invention will now be described in more detail with reference to the following examples.

EXAMPLES

Monomers: VP: (International Specialty Products). DMAPMA: (Rohm America). Crosslinkers: Pentaerythritol triallyl ether (PTE), $HOCH_2-C(-CH_2-O-CH_2-CH=CH_2)_3$ and methylene-bis-acrylamide (BIS), (Aldrich). Initiators: tertiary butyl peroxy pivalate (Lupersol® 11) and tertiary amyl peroxy pivalate (Lupersol® 554), (Lucidol). Solvent: Deionized water. Non-solvent: Heptane, (Aldrich).

EXAMPLE 1

Preparation of XL-PVP/DMAPMA Cationic Hydrogel of Invention

The optimized reaction cycling time is very short (1.5 hours at 60° C. and 4 hours at 85° C.). The process includes the steps of:

(1) Clean, dry, and tare a 1-liter glass resin reaction flask.
(2) Install the reactor with agitator, heating mantle, condenser, thermocouple, septum for initiator addition, and nitrogen purging.
(3) Add part of water solvent, all VP monomer, all DMAPMA monomer, all the BIS crosslinker, and all the Lupersol® 11 initiator, into the reactor.

The VP/DMAPMA ratio will vary depending on the kind of hydrogel to be made. A preferred initial concentration of VP and DMAPMA in the system is 20% by weight. The preferred weight ratio of crosslinker to VP and DMAPMA is 0.20%. The preferred weight ratio of Lupersol® 11 to VP and DMAPMA is 1.10%.

(4) At room temperature, start a purge with nitrogen until the reaction is complete.
(5) Raise the temperature to 60° C. and maintain for 1.5 hours.
(6) During the 60° C. period, when gelation occurs and the system is too viscous to agitate, add water to dilute the system from 20% to 10% solids.
(7) Raise the temperature to 85° C. and maintain for 4 hours to reduce the residual monomer level.
(8) When reaching 85° C., directly inject Lupersol® 554 hourly through the syringe and rubber septum on the top of reactor into the reaction mixture. Four (4) additions of Lupersol® 554 as booster are sufficient to reduce the residual monomer to acceptable levels.
(9) During the 85° C. heating period, when the system is too viscous to agitate, all water to further dilute the system from 10% to 7.5% solids.
(10) When the reaction is complete, cool the system to room temperature, and transfer the product into a large beaker.
(11) A Ross Homogenizer is used to break up the gel. Addition of water to further dilute the system to 5% solids is used to enable the product to flow in and out of the homogenizer.

Brookfield Viscosity Measurements

The viscosity of aqueous copolymer solutions were measured with a Brookfield Digital Viscometer.

The XL-PVP/DMAPMA copolymer hydrogels of the invention have a low viscosity at high pH, where the amines are essentially uncharged. However, upon addition of a suitable acid, the pH drops and positive charges are generated on the polymer side chains as the amine monomer is protonated. The repulsion forces developed between these positive charges causes the polymer to swell, enabling the cationic hydrogel to be used effectively as a thickener at a low pH.

Swelling Volume Measurements

A 1% (w/v) aqueous solution was stoppered in a 100 ml graduated cylinder and allowed to stand at room temperature for 2 days. The volume attained by the gel was recorded as the swelling volume with the units of ml/g.

The cationic hydrogel of this invention shows an extremely high capacity for adsorbed water. For example, 0.01 g of dry XL-PVP/DMAPMA adsorbs 1.7 grams of deionized water, which is 170 times its weight.

EXAMPLE 2

Conditioning Shampoo Formulation

Part A (% By Weight)
15 Ammonium Lauryl Sulfate (Standapol® A, Henkel Corporation)
15 Sodium Lauryl Sulfate (Rhodaon® SB-8208/S, Rhône Poulenc)
8 Cocamidopropyl Betaine (Mirtaine® CB, Rhône Poulenc)
2 Lauramide DEA (Monamid® 716, Mona Industries)
Part B (% By weight)
1 Cationic hydrogel of Invention as Conditioning Additive
58.8 Deionized $H_2O$
Part C (% By Weight)
0.2 Diazolidinyl Urea/Iodopropynyl Butylcarbamate (Germall® Plus, ISP)

Instructions

Heat Part A to 60° C. with moderately slow stirring for approximately ½ hour or until solution becomes transparent. At the same time, heat Part B to 55° C. while stirring until homogeneous solution is obtained. Add Part B to Part A while continuously stirring. Remove temperature source. Once the resulting solution has reached 45° C., add Part C. Continue to stir (slowly) until the target solution has cooled to an ambient temperature.

Figure 1:
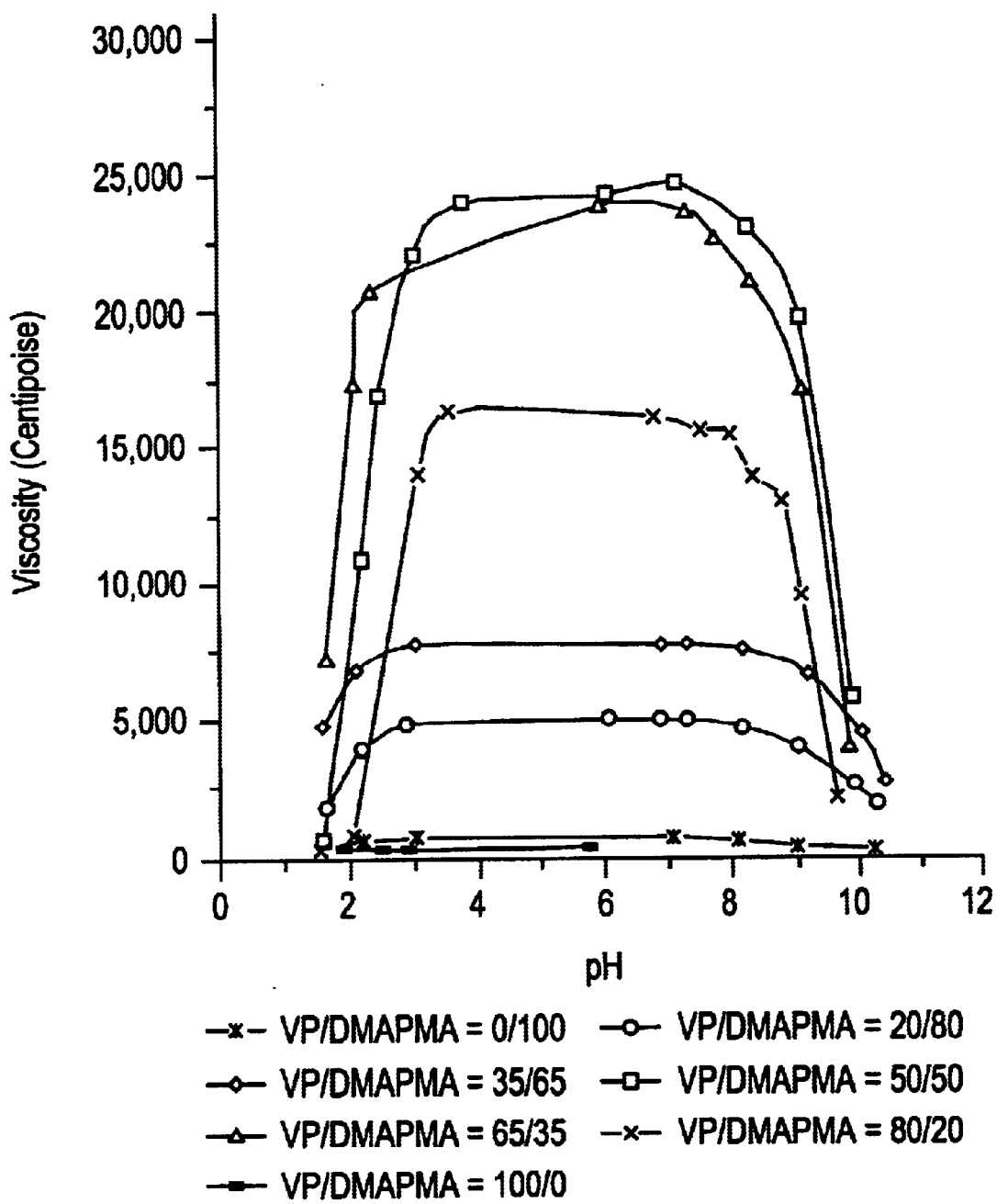
FIG. 1 is a plot of viscosity in cps vs. pH adjusted with HCl for XL-PVP/DMAPMA cationic copolymer hydrogels of invention at a solids content of 1%, at various monomer ratios, the crosslinker being present in an amount of 0.2% by weight of monomers.
Figure 2:
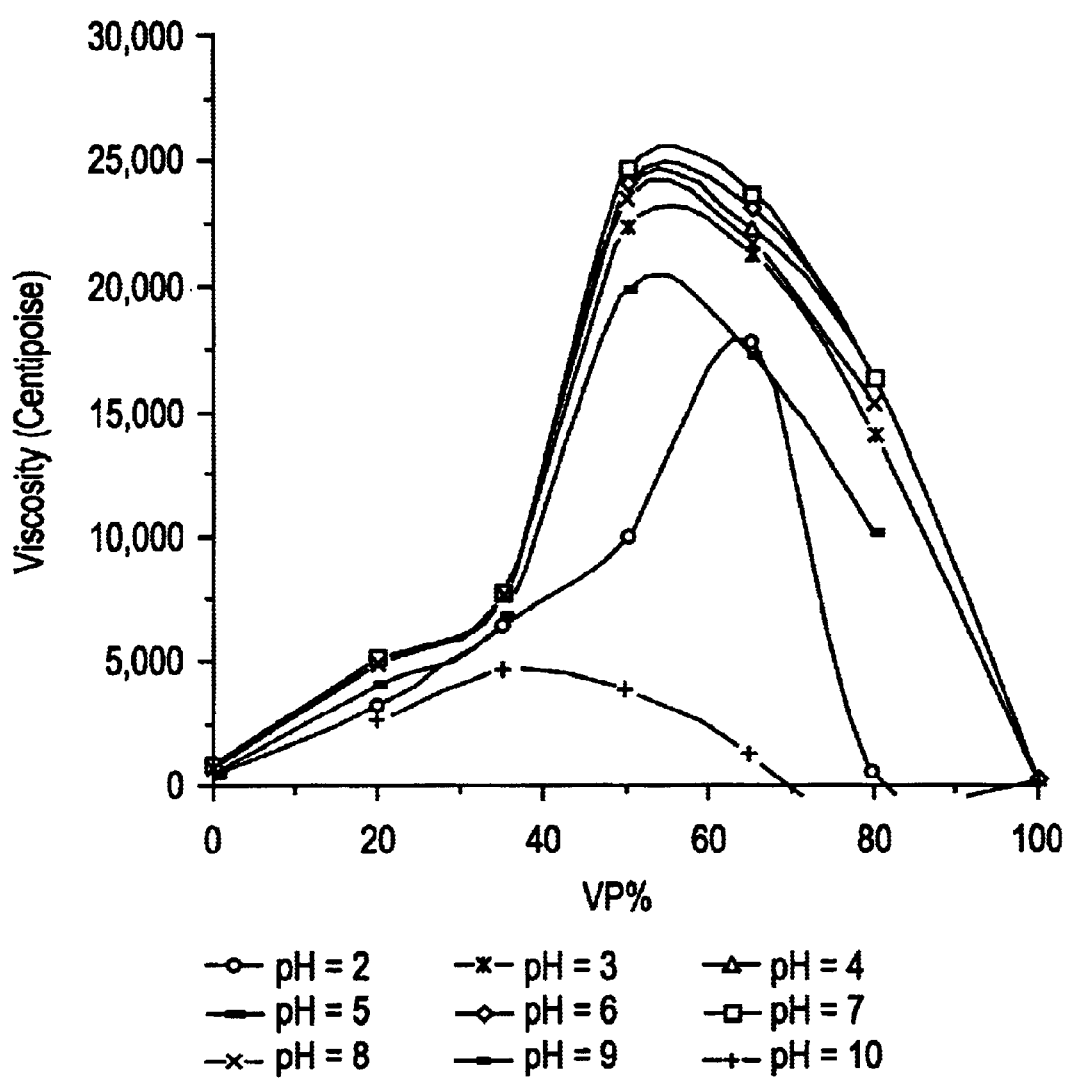
FIG. 2 is a plot of viscosity in cps vs. % VP in XL-PVP/DMAPMA cationic copolymer hydrogel at a solids content of 1%, crosslinker 0.20% by weight of monomers, at various pHs.
Figure 3A:
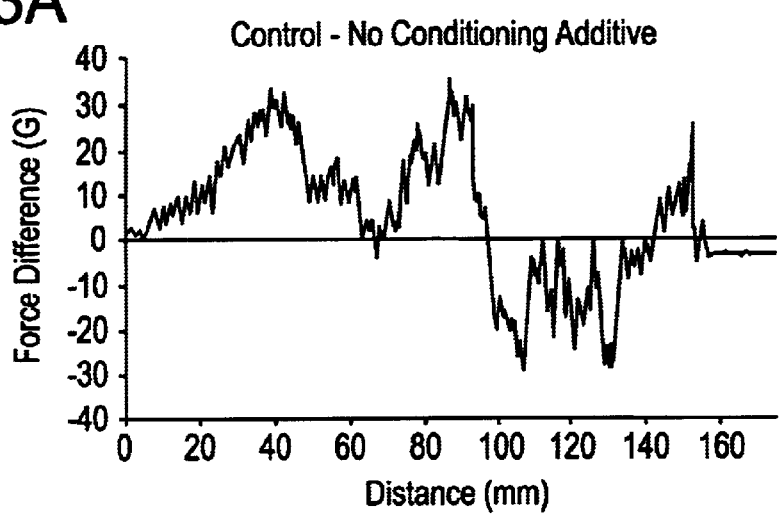
FIG. 3 shows curves of differential force combing (G) vs. distance (nm) along hair tresses for virgin hair treated with a control shampoo FIG. 3($a$), shampoo containing Polymer JR FIG. 3($b$), and shampoo containing the cationic hydrogel of this invention FIG. 3($c$).
Figure 3B:
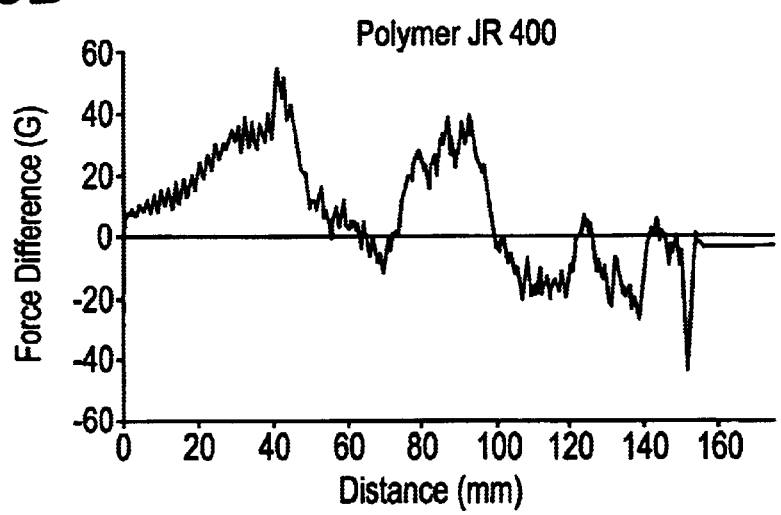
Figure 3C:
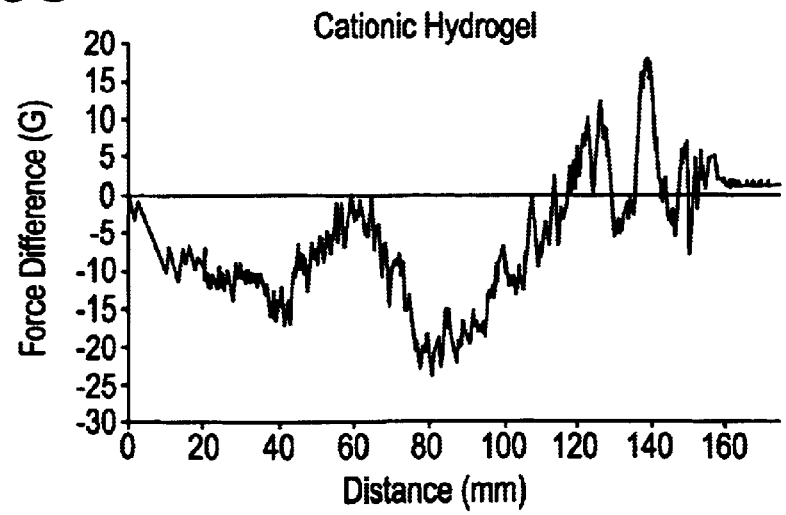

The combing curves for control and Polymer JR shampoo in FIGS. 3(a) and (b) show two maxima at about 40 and 85 nm. In contrast, hair treated with a shampoo containing the cationic hydrogel of this invention, FIG. 3(c), shows two minima in the same positions. Thus, this data demonstrates the conditioning effect of the cationic hydrogel of this invention when applied from a shampoo base.

As shown in FIG. 4 in the case of hair treated with shampoos containing the cationic hydrogels of this invention (Tresses 1 and 2), the fibers are glued together in the treated areas, with the effect particularly strong for Sample #1 polymer (Tress #1). This demonstrates the styling effect of the cationic hydrogel.

Effective hair care compositions can be made with the crosslinked cationic hydrogel of the invention. In such formulations, the crosslinked hydrogel dispersion provides relatively thick and lubricious layers on the surface of hair. Unlike linear, uncrosslinked cationic polymers, which lay flat on the hair surface, the swollen hydrogel particles of the crosslinked copolymer forms thick deposits which significantly modify the surface properties of hair.

The invention copolymer also can be used effectively in anionic surfactant-based shampoo compositions which ordinarily do not provide a favorable medium for deposition of linear cationic polymers or surfactants. The XL-PVP/DMAPMA copolymer, in contrast, when used, for example, as a 1% solution, provides excellent conditioning as evidenced by wet and dry combing evaluations. Specifically, shampoo compositions containing 0.5% copolymer showed a significantly better conditioning performance than linear cationic polymers such as Styleze® CC-10 or Polymer JR® 400. In addition, the deposited copolymer layer from the hydrogel of the invention also provides links between fibers after drying, thus resulting in a styling or fixative effect, which remains intact even after repeated rinsing with water after shampooing.

Conditioning and styling properties on hair can also be obtained with cationic hydrogels of the following copolymers:

XL-acrylamide/DMAPMA, XL-poly(vinyl caprolactam) (PVCL)/DMAPMA and XL-acrylamide/dimethylaminoethyl methacrylate (DMAEMA).

While the invention has been described with particular reference to certain embodiments thereof, it will be understood that changes and modifications may be made which are within the skill of the art. Accordingly, it is intended to be bound only by the following claims, in which:

What is claimed is:

1. A stable, aqueous flowable cationic homogenized hydrogel consisting essentially of, by weight, 1–50% of a crosslinked cationic copolymer of 40–70% vinylpyrrolidone (VP) and 30–60% 3-dimethylaminopropyl(meth)acrylamide (DMAPMA) monomers, a crosslinking agent in an amount of 0.05–1% of said monomers, and water, said homogenized hydrogel having a pH of about 10, a Brookfield viscosity of about 650 (RV spindle #3, speed 10 rpm), and is capable of increasing its viscosity up to 40× at a pH of 3–9, and of absorbing up to 200× its weight of water, and of effectively conditioning hair in the presence of an anionic surfactant.

2. A cationic hydrogel according to claim 1 in which said crosslinking agent is present in an amount of 0.1–0.5%.

3. A cationic hydrogel according to claim 2 in which said amount is 0.2%.

4. A cationic hydrogel according to claim 1 wherein said copolymer comprises 50–65% VP and 35–50% DMAPMA.

5. A cationic homogenized hydrogel according to claim 1 with 5–20% of said copolymer therein.

6. A cationic homogenized hydrogel according to claim 5 with 1–5% of said copolymer therein.

7. A composition comprising the homogenized hydrogel of claim 1, at a pH of 3–9, as a viscosity modifier therein, which can provide a Brookfield viscosity for said composition of at east 10,000 cps at 1% copolymer solids.

8. A composition according to claim 7 wherein said pH is 4–8.

9. A hair treatment composition comprising about 0.01–5% by weight of the cationic hydrogel of claim 1, and an anionic surfactant, for conditioning, styling and cleansing.

10. An aqueous solution polymerization process of making the flowable cationic homogenized hydrogel of claim 1 which comprises forming a mixture, by weight, of 1–50% of a blend of 40–70% VP and 30–60% DMAPMA monomers, 0.1–0.5% crosslinker, water and initiator, polymerizing the mixture with agitation at a temperature of about 60° C. for about 1½ hours, then at 85° C. to reduce residual monomers, optionally adding water periodically to reduce the solids content of the product, and homogenizing the product to form a flowable cationic homogenized hydrogel.

11. A process according to claim 10 wherein said copolymer contains about 20% of a mixture of 50–65% VP, 35–50% DMAPMA and about 0.2% crosslinker.

12. A process according to claim 11 wherein water is added periodically to reduce the solids content to about 5%.

13. A product of the process of claim 10.

* * * * *